(12) United States Patent
Cauldwell et al.

(10) Patent No.: US 11,957,343 B2
(45) Date of Patent: Apr. 16, 2024

(54) SURGICAL FASTENERS FOR ARTICULATING SURGICAL INSTRUMENTS

(71) Applicant: C.R. Bard, Inc., Murray Hill, NJ (US)

(72) Inventors: Nathan Stewart Cauldwell, Hope, RI (US); Augustus Felix, Cranston, RI (US); Derek Affonce, Uxbridge, MA (US); Kevin J. Ranucci, Warwick, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 484 days.

(21) Appl. No.: 17/174,511

(22) Filed: Feb. 12, 2021

(65) Prior Publication Data

US 2021/0161528 A1   Jun. 3, 2021

Related U.S. Application Data

(62) Division of application No. 15/867,063, filed on Jan. 10, 2018, now Pat. No. 10,932,776.

(51) Int. Cl.
*A61B 17/072* (2006.01)
*A61B 17/00* (2006.01)
(Continued)

(52) U.S. Cl.
CPC ...... *A61B 17/07207* (2013.01); *A61B 17/068* (2013.01); *A61B 17/846* (2013.01);
(Continued)

(58) Field of Classification Search
CPC ............ A61B 17/068; A61B 17/07207; A61B 17/846; A61B 17/8872; A61B 2017/003;
(Continued)

(56) References Cited

U.S. PATENT DOCUMENTS

| 4,873,976 A | 10/1989 | Schreiber |
| 5,810,825 A | 9/1998 | Huebner |

(Continued)

FOREIGN PATENT DOCUMENTS

| CN | 102271596 A | 12/2011 |
| CN | 102448388 A | 5/2012 |

(Continued)

OTHER PUBLICATIONS

International Search Report and Written Opinion for International Application No. PCT/US2019/012135, dated May 28, 2019.

(Continued)

*Primary Examiner* — Mohamed G Gabr

(74) *Attorney, Agent, or Firm* — Wolf, Greenfield & Sacks, P.C.

(57) ABSTRACT

Surgical fasteners for use with articulating surgical instruments are disclosed. In one embodiment, a surgical fastener may include a head, a shaft extending distally from the head, and a through bore extending through the shaft from a proximal surface of the head to a distal end of the shaft. A fastener carrier of a surgical instrument may be slidably received in the through bore, and the through bore may be sized and shaped to have two or fewer contact points with the fastener carrier when the fastener carrier is in a fully articulated configuration. In another embodiment, a fastener may include a head, a shaft extending distally from the head and including a distal tip, a sloped surface sloping toward the distal tip, and a through bore passing through the head, shaft, and sloped surface. The sloped surface may terminate at two shoulders located on opposing sides of the through bore.

26 Claims, 8 Drawing Sheets

(51) Int. Cl.
*A61B 17/064* (2006.01)
*A61B 17/068* (2006.01)
*A61B 17/84* (2006.01)
*A61B 17/88* (2006.01)
*A61B 90/00* (2016.01)

(52) U.S. Cl.
CPC .... *A61B 17/8872* (2013.01); *A61B 2017/003* (2013.01); *A61B 2017/00309* (2013.01); *A61B 2017/00327* (2013.01); *A61B 2017/00367* (2013.01); *A61B 2017/0647* (2013.01); *A61B 2017/07221* (2013.01); *A61B 2017/07228* (2013.01); *A61B 2090/0803* (2016.02)

(58) Field of Classification Search
CPC ........... A61B 2017/00309; A61B 2017/00327; A61B 2017/00367; A61B 2017/0647; A61B 2017/07221; A61B 2017/07228; A61B 2090/0803
See application file for complete search history.

(56) References Cited

U.S. PATENT DOCUMENTS

| | | | |
|---|---|---|---|
| 6,779,701 | B2 | 8/2004 | Bailly et al. |
| 7,758,612 | B2 | 7/2010 | Shipp |
| 8,216,272 | B2 | 7/2012 | Shipp |
| 8,663,244 | B2 | 3/2014 | Reeser |
| 10,251,642 | B2 | 4/2019 | Ranucci et al. |
| 10,327,775 | B2 | 6/2019 | Ranucci et al. |
| 10,932,776 | B2 | 3/2021 | Cauldwell et al. |
| 2001/0041937 | A1 | 11/2001 | Rieser et al. |
| 2003/0181800 | A1 | 9/2003 | Bonutti |
| 2006/0217727 | A1 | 9/2006 | Munro et al. |
| 2006/0276841 | A1 | 12/2006 | Barbieri et al. |
| 2009/0204130 | A1 | 8/2009 | Kantsevoy et al. |
| 2010/0222827 | A1 | 9/2010 | Griffiths et al. |
| 2010/0312258 | A1 | 12/2010 | Shipp |
| 2011/0006104 | A1 | 1/2011 | Felix |
| 2012/0029538 | A1 | 2/2012 | Reeser |
| 2013/0144334 | A1 | 6/2013 | Bouduban et al. |
| 2014/0276964 | A1* | 9/2014 | Ranucci ............... A61B 17/064 606/139 |
| 2014/0276965 | A1 | 9/2014 | Ranucci et al. |
| 2015/0216521 | A1* | 8/2015 | Deitch ................ A61B 17/064 606/232 |
| 2016/0338698 | A1 | 11/2016 | Cardinale et al. |
| 2016/0354081 | A1 | 12/2016 | Ranucci et al. |
| 2017/0020523 | A1 | 1/2017 | Ranucci et al. |
| 2017/0087697 | A1 | 3/2017 | Garcia et al. |
| 2019/0167261 | A1 | 6/2019 | Ranucci et al. |
| 2019/0209170 | A1 | 7/2019 | Cauldwell et al. |
| 2019/0269406 | A1 | 9/2019 | Ranucci et al. |

FOREIGN PATENT DOCUMENTS

| | | |
|---|---|---|
| CN | 104546040 A | 4/2015 |
| CN | 106102618 A | 11/2016 |
| CN | 107303189 A | 10/2017 |
| DE | 103 00 787 | 9/2004 |
| EP | 2 012 677 A1 | 11/2011 |
| EP | 3 235 443 A1 | 10/2017 |
| JP | 2006-528895 A | 12/2006 |
| JP | 2013-56164 A | 3/2013 |
| JP | 2017-131765 A | 8/2017 |
| WO | WO 97/18761 A1 | 5/1997 |
| WO | WO 2007/098512 A1 | 9/2007 |

OTHER PUBLICATIONS

U.S. Appl. No. 16/416,377, filed May 20, 2019, Ranucci et al.
U.S. Appl. No. 16/268,596, filed Feb. 6, 2019, Ranucci et al.
PCT/US2019/012135, May 28, 2019, International Search Report and Written Opinion.

* cited by examiner

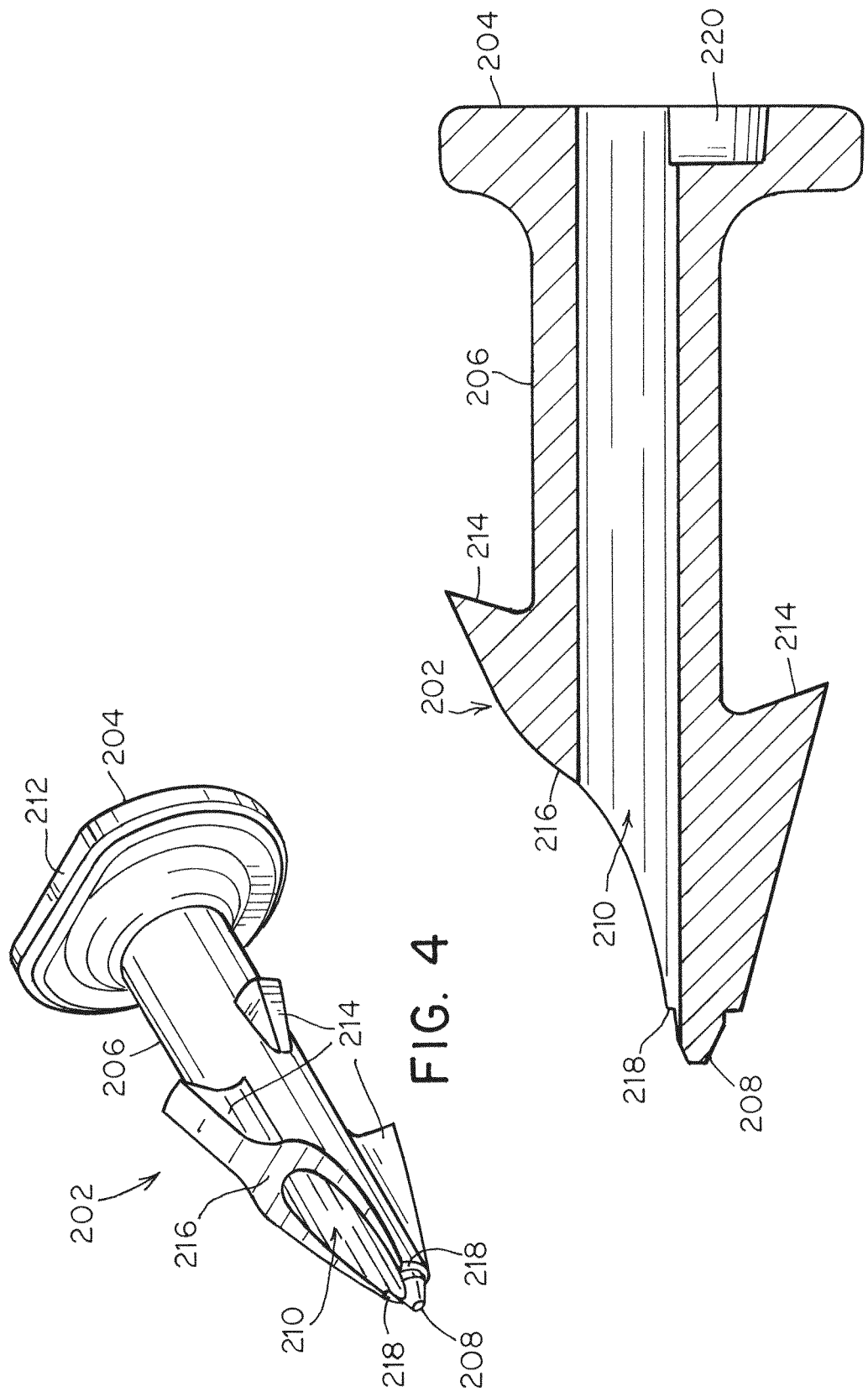

SURGICAL FASTENERS FOR ARTICULATING SURGICAL INSTRUMENTS

CROSS-REFERENCE TO RELATED APPLICATIONS

This application is a divisional application of U.S. application Ser. No. 15/867,063, filed on Jan. 10, 2018, which is incorporated herein by reference in its entirety.

FIELD

Disclosed embodiments are related to surgical fasteners for use with articulating surgical instruments.

BACKGROUND

A surgical mesh fabric or other prosthetic repair fabric may be used to surgically repair a hernia. The prosthetic repair fabric is typically placed in an open procedure or laparoscopically. Oftentimes a surgical instrument is used to secure the repair fabric in place by deploying one or more fasteners from a distal end of the surgical instrument through the prosthetic repair fabric and into the underlying tissue. However, a surgical instrument that includes a rigid elongated shaft assembly for deploying the fasteners may have a limited range of motion within the surgical field. Consequently, many surgical instruments include at least one articulable portion along the elongated shaft assembly to facilitate the orientation and placement of fasteners within the surgical field.

SUMMARY

In one embodiment, a surgical instrument includes a fastener carrier extending distally from a handle of a surgical instrument, and the fastener carrier is movable between a non-articulated configuration and a fully articulated configuration. The surgical instrument further includes a fastener provided on the fastener carrier, and the fastener includes a head, a shaft extending distally from the head, and a through bore extending through the shaft from a proximal surface of the head to a distal end of the shaft. The fastener carrier is slidably received in the through bore, and the through bore is sized and shaped to have two or fewer contact points with the fastener carrier when the fastener carrier is in the fully articulated configuration.

In another embodiment, a method of operating a surgical instrument includes moving a fastener carrier from a non-articulated configuration to a fully articulated configuration. The fastener carrier extends distally from a handle of a surgical instrument, and a fastener is provided on the fastener carrier. The fastener includes a head, a shaft extending distally from the head, and a through bore extending through the shaft from a proximal surface of the head to a distal end of the shaft. The fastener carrier is slidably received in the through bore. The method further includes contacting the through bore with the fastener carrier at two or fewer contact points when the fastener carrier is in the fully articulated configuration.

In a further embodiment, a surgical fastener includes a head, a shaft extending distally from the head and including a distal tip, a sloped surface sloping toward the distal tip, and a through bore passing through the head, the shaft, and the sloped surface. The sloped surface terminates at two shoulders located on opposing sides of the through bore, and the distal tip extends distally away from the two shoulders of the sloped surface.

In yet another embodiment, a surgical fastener includes a head, a shaft extending distally from the head, and a through bore extending through the shaft from a proximal surface of the head to a distal end of the shaft. The through bore has a first transverse dimension at a proximal end of the through bore and a second transverse dimension at a distal end of the through bore, and the first transverse dimension is smaller than the second transverse dimension.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 4 is a perspective view of one embodiment of a surgical fastener;

FIG. 5 is a cross-sectional side view of the surgical fastener of FIG. 4;

DETAILED DESCRIPTION

Figure 1:
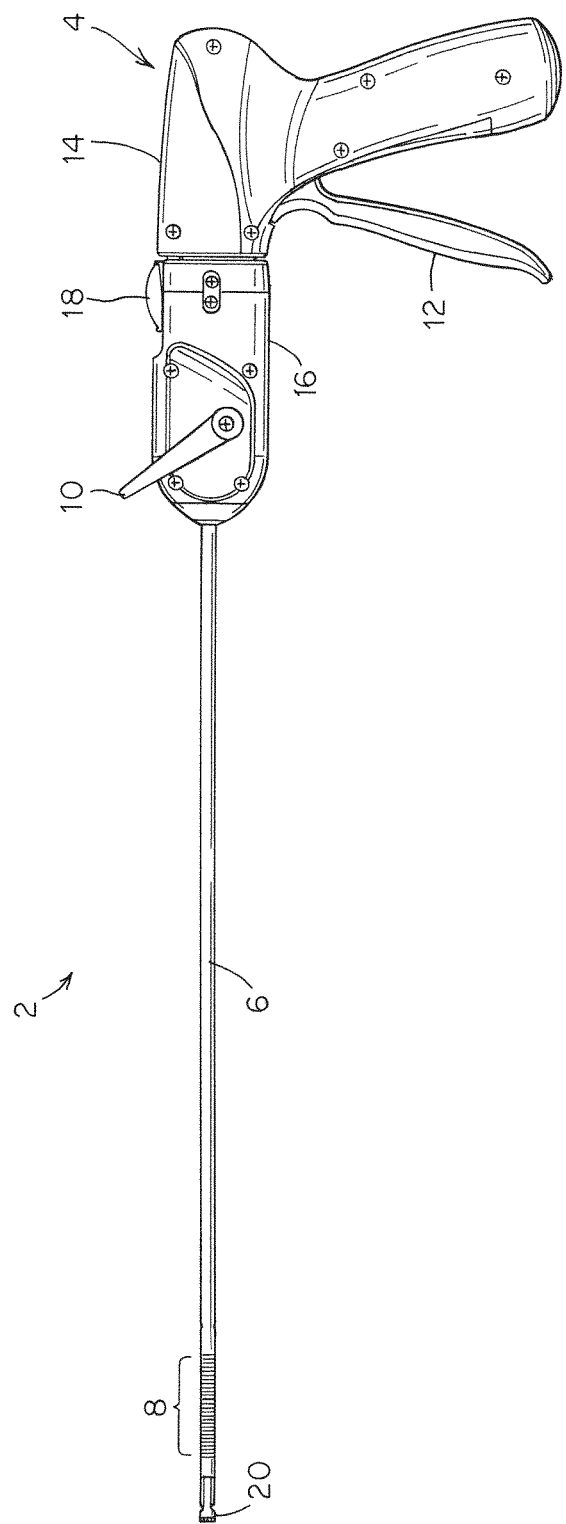
FIG. 1 is a schematic representation of one embodiment of an articulable surgical instrument.

The inventors have appreciated numerous benefits associated with surgical instruments that include an elongated shaft assembly having an articulable portion to allow at least a portion of the surgical instrument to be placed in one or more desired configuration and/or orientations. For example, articulation of the articulable portion may allow a distal tip of the elongated shaft assembly to be easily placed at desired position(s) and/or orientation(s) for performing a surgical procedure, such as deploying a surgical fastener into tissue. In some embodiments, the articulation of the articulable portion may involve bending the articulable portion such that the articulable portion is in a curved configuration when articulated. In view of the foregoing, the inventors have appreciated numerous benefits associated with surgical fasteners for use with articulating surgical instruments.

According to some aspects of the current disclosure, the inventors have appreciated that it may be desirable to provide fasteners including one or more features to avoid binding of the fasteners within an elongated shaft assembly of a surgical instrument as the fasteners are deployed out of the surgical instrument when the surgical instrument is in an articulated configuration. Including these types of feature may facilitate the fasteners being deployed easily when the elongated shaft assembly is articulated. In some embodiments, a fastener includes a head, a shaft extending distally from the head, a distal tip, and a through bore extending through the shaft from a proximal surface of the head to a distal portion and/or end of the shaft. The inventors have recognized that contact between a fastener carrier and the through bore of the fastener (through which the carrier is received) may inhibit movement of the fastener relative to the elongated shaft assembly and/or deployment of the fastener. Accordingly, in some embodiments, the fastener though bore and fastener carrier may be constructed and arranged to have two or fewer contact points with the fastener carrier when the surgical instrument (including the fastener carrier) is in the articulated configuration. Without wishing to be bound by theory, such a configuration may permit the fasteners to freely slide along the fastener carrier without binding when the fastener carrier is articulated (e.g., curved).

In some embodiments, a plurality of fasteners may be provided as a fastener stack within an elongated shaft assembly. Accordingly, the inventors have appreciated benefits associated with a fastener structure that permits the fastener stack to easily accommodate a curved configuration associated with the elongated shaft assembly being articulated. In one embodiment, each fastener may include a cavity formed on the proximal surface of the head. The cavity may be offset relative to a central axis of the fastener and constructed and arranged to receive the distal tip of an adjacent fastener in the fastener stack. When the surgical instrument is articulated, the distal tips of the fasteners may move within the cavities, which may allow the adjacent fasteners to move relative to one another to accommodate the articulated configuration without applying pressure to the pointed distal tips of the surgical fasteners located within the recesses.

In addition to the above, the inventors have recognized that fasteners including through bores that extend through a shaft of the fasteners may include thin structures that are oriented in a distal direction and that may be deformed when the fasteners are deployed distally into tissue Accordingly, the inventors have appreciated that maintaining the dimension of features located adjacent to a through bore of the surgical fastener above a minimum feature size may limit, and in some instances prevent, deformation of the surgical fasteners during deployment. For example, in one embodiment, the shaft and through bore of a fastener may terminate at a sloped surface adjacent a distal tip of the surgical fastener, and a minimum dimension of portions of the surgical fastener surrounding the distal portion of the through bore may be maintained above the a noted minimum features size.

As used herein, the term "distal direction" within a surgical device may refer to a direction that extends along a central longitudinal axis of a surgical device towards a distal end of the surgical device where a desired operation is performed. Correspondingly, a "proximal direction" may refer to a direction that is directed in an opposite direction relative to the distal direction such that it may be directed along the central longitudinal axis of the surgical device away from the surgical device's distal end where the desired operation is performed.

The surgical fasteners and surgical devices described herein may be made out of any desirable material or combination of materials including, but not limited to, various types of metals and polymers. In some instances, the surgical fasteners described herein may be made from materials that are either sterilized and/or are sterilizable using any appropriate method including, but not limited to, heat, radiation, and/or pressure. Moreover, the materials may be capable of either being sterilized before, during, or after assembly and packaging to maintain sterility.

According to some embodiments, an articulating surgical instrument (from which surgical fasteners may be deployed) may include an elongated shaft assembly that extends distally from a handle of a surgical instrument. The elongated shaft assembly includes an articulable portion that may articulate in at least one direction between a first position, which may correspond to a non-articulated configuration, to a second position, which may correspond to a fully articulated configuration in which the distal tip is oriented at an angle (e.g., an articulation angle) relative to a portion of the elongated shaft assembly located proximal to the articulable portion. When in the non-articulated configuration, a longitudinal axis passing through the articulable portion may be aligned with a longitudinal axis of the proximal portion of the elongated shaft assembly. Correspondingly, when in the fully articulated configuration, the distal tip of the elongated shaft assembly, and the longitudinal axis of the articulable portion, is oriented at an articulation angle relative to the longitudinal axis of the proximal portion. In one embodiment, the articulation angle of the fully articulated configuration may be between −30 degrees and 30 degrees, between −45 degrees and 45 degrees, between −90 degrees and 90 degrees, between −180 degrees and 180 degrees, 15 degrees and 90 degrees, or 45 degrees and 90 degrees, though it should be understood that the current disclosure is not limited to any particular range of articulation angles. Moreover, in some embodiments, the articulable portion may be movable to one or more additional articulated positions between the non-articulated (i.e., straight) configuration and the fully articulated configuration.

For the sake of clarity, the currently disclosed embodiments discussed below in regards to the figures are directed to a laparoscopic device for deploying one or more fasteners. However, the current disclosure is not limited to laparoscopic devices for deploying one or more fasteners. Instead, the disclosed articulation systems, locking mechanisms, controls, and surgical fasteners may be used in any appropriate surgical instrument including an articulable portion. For example, appropriate surgical instruments may include an endoscopic device, a borescopic device, a catheter, a surgical instrument for use in "open" procedures, or any other appropriate surgical instrument. Further, the disclosed surgical instruments may include any appropriate end effector and are not limited to the deployment of fasteners.

However, in those embodiments including fasteners, the instrument including the articulation locking mechanism may be loaded with one or more fasteners, or it may be constructed to allow the user to load the instrument with one or more fasteners.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 depicts one embodiment of a surgical instrument 2. The surgical instrument includes a handle 4 and an elongated shaft assembly 6 extending distally from the handle toward a distal end 20, from which fasteners may be deployed. The elongated shaft assembly 6 includes an articulable portion 8 that is moveable between a non-articulated (i.e., straight) position, and one or more articulated (i.e., curved or bent) positions. Articulation of the articulable portion 8 may be controlled by an articulation control 10, such as a rotatable and/or axially displaceable knob, handle, lever, or other feature which may be moved relative to the handle 4 between one or more positions to move the articulable portion 8 between the non-articulated configuration and the one or more articulated configurations. The surgical instrument 2 also includes a trigger 12 for actuating a fastener deployment system to deploy a fastener, though other appropriate types of actuation systems to perform other types of operations are also contemplated.

The articulable portion 8 of the elongated shaft assembly may be moved between at least a first position, such as an unarticulated (i.e. straight) position, and second position, such as a fully articulated position (e.g., a curved configuration), using the articulation control 10. Depending on the embodiment, the articulable portion 8 may be moved to one or more preselected articulation angles, or the articulable portion 8 may be adjusted to one or more arbitrary (i.e. not preselected) articulation angles. The articulable portion 8 may be articulated in at least a first direction, though embodiments in which the articulable portion articulates in at least a second direction are also envisioned. For example, the articulable portion 8 may be articulated in a first direction corresponding to an articulation angle greater than approximately 0° and in an opposing second direction corresponding to an articulation angle less than approximately 0°. Alternatively, or in addition to the above, the articulable portion 8 might be articulated about two different axes (e.g. articulation in the horizontal direction and the vertical direction) such that it articulates in at least two directions.

In some embodiments, it may be desirable to rotate the elongated shaft assembly 6 to facilitate positioning of the distal tip. For example, the elongated shaft assembly 6 may simply be adapted to be rotatable relative to at least a portion of the handle 4. Alternatively, a portion of the handle 4 including the elongated shaft assembly 6 may be rotatable relative to another portion of the handle 4, such as the portion including the grip. One such embodiment is depicted in FIG. 1. In the depicted embodiment, the surgical instrument 2 includes a first handle portion 14 and a second handle portion 16 from which the elongated shaft assembly 6 extends. The first and second handle portions 14 and 16 may be constructed and arranged in any appropriate fashion to be rotatable relative to one another. The surgical instrument may include a rotation lock 18 that is movable to selectively permit and prevent rotation of the second handle portion 16 relative to the first handle portion 14. It should be understood that while a surgical instrument including a rotatable elongated shaft assembly 6 or handle 4 is depicted in the figures, a surgical instrument including a unitary handle and/or an elongated shaft assembly 6 that is stationary relative to the handle are also possible as the current disclosure is not limited in this manner.

In certain applications, it may be advantageous to include a distal rigid straight portion 20 that is distally located from the articulable portion 8 of the elongated shaft assembly. The rigid straight portion 20 may include a number of features to aid in the deployment of fasteners from the distal end of the elongated shaft assembly 6. For example, the distal rigid straight portion 20 may include fastener retaining elements such as tabs to retain a distal most fastener in a fastener deployment position prior to actuation of the surgical instrument. Additionally, without wishing to be bound by theory, when a driveshaft of a fastener deployment system applies a force to a fastener as it goes around an articulated portion of the elongated shaft assembly, the force applied by the drive shaft to the head of the fastener may not be fully aligned with the deployment direction of the associated fastener. For example, a distal-most fastener may be located distally relative to a distal end of the driveshaft, and correspondingly, the fastener may be located within a portion of the elongated shaft assembly that is oriented at an angle that is larger than a portion containing the distal end of the drive shaft. Consequently, when the drive shaft applies a force to the fastener (e.g., via reciprocal movement of the driveshaft), the force applied to the fastener may be misaligned with a longitudinal axis of the fastener.

Figure 3:
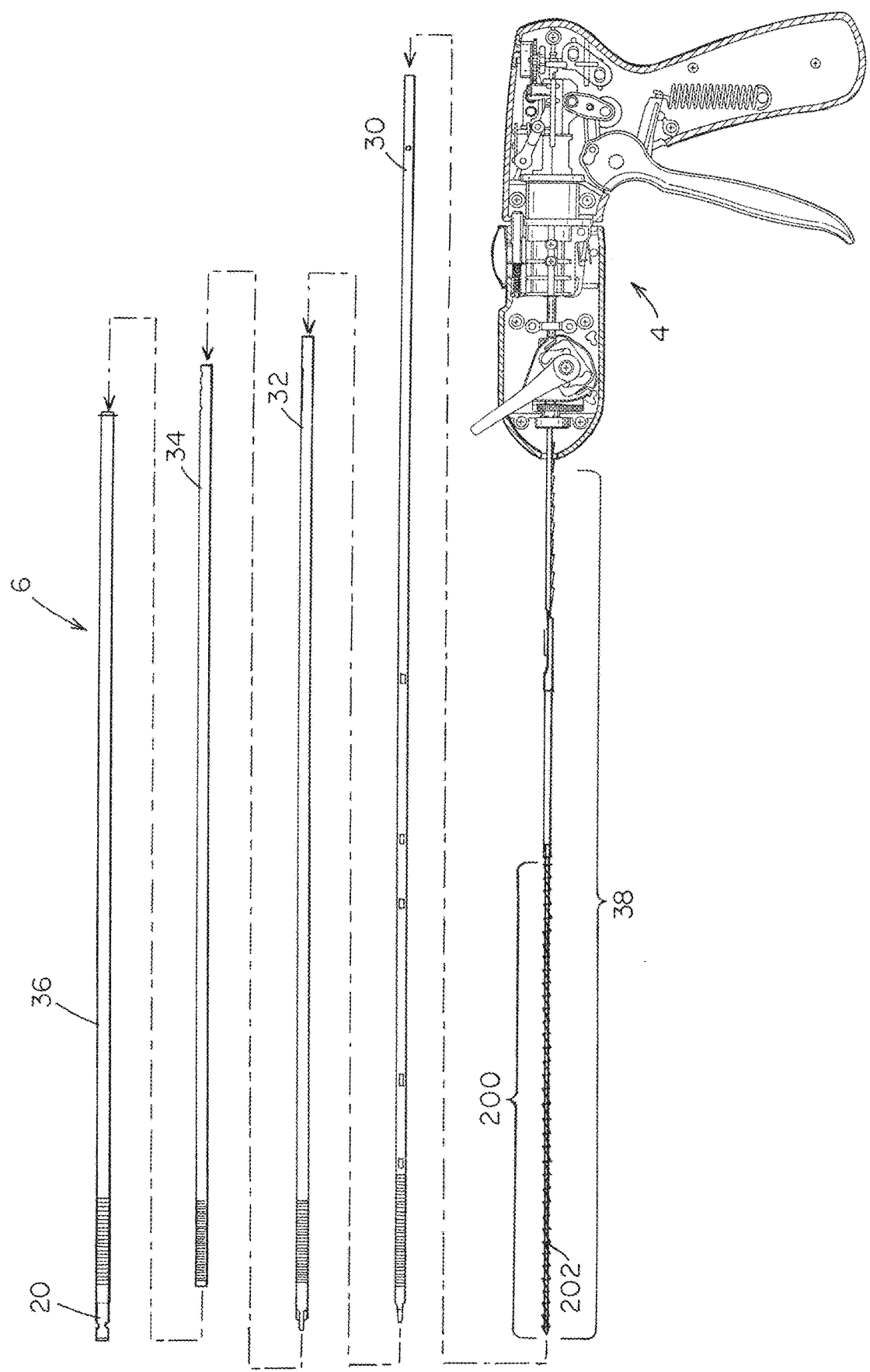
FIG. 3 is an exploded view of the elongated shaft assembly of the surgical instrument of FIG. 1.

In view of the foregoing, it may be desirable to include the distal rigid straight portion 20 to provide a straight portion of the elongated shaft assembly with a sufficient length to accommodate at least one fastener and to permit the actuation force from the fastener deployment system to be applied to that fastener in the same direction as the fastener deployment direction. Without wishing the bound by theory, this may result in reduced actuation forces required to deploy a fastener from the surgical instrument. In some embodiments, the length of the distal rigid straight portion may be equal to or greater than a length of a fastener such that the distal end of the driveshaft may be aligned in the deployment direction. For example, as illustrated in FIG. 3, the distal rigid straight portion 20 is longer than the length of the fasteners 202. In this manner, both a distal-most fastener and the distal end of the driveshaft may be received in the distal rigid straight portion to aid in aligning the deployment force from the driveshaft with the orientation of the fastener. While a surgical instrument 2 including a distal rigid straight portion 20 has been described herein, and depicted in the figures, it should also be understood that embodiments are envisioned in which the articulable portion 8 extends all the way to the distal end of the elongated shaft assembly 6 such that the surgical instrument does not include a distal rigid straight portion.

Figure 2:
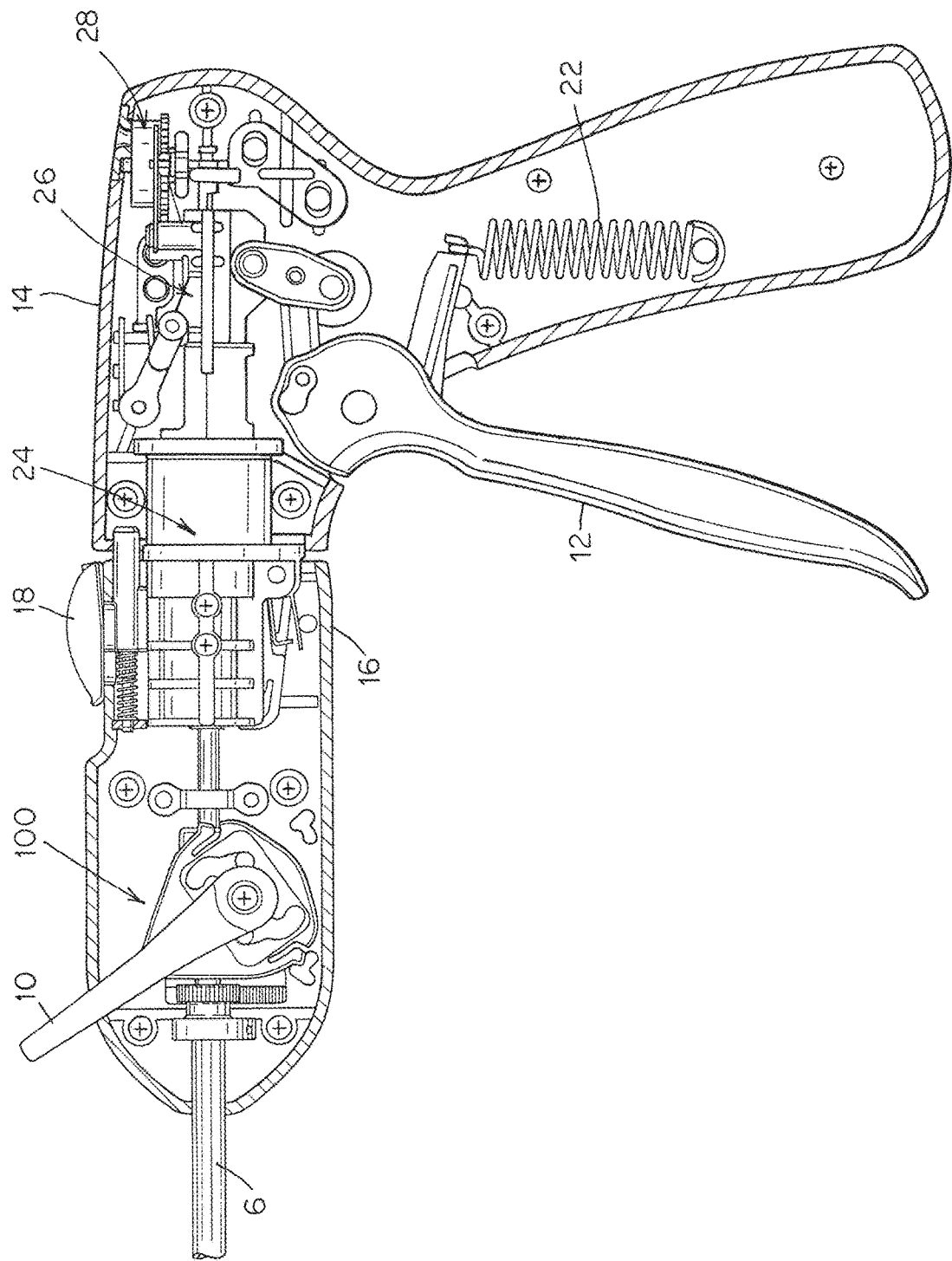
FIG. 2 is a side view of an interior portion of the articulable surgical instrument of FIG. 1.

FIG. 2 is a schematic side view of the surgical instrument of FIG. 1, showing the various components and systems that may be provided within the handle 4. As illustrated, the trigger 12 may be coupled to a return spring 22, which may provide a restoring force to urge the trigger back towards an unactuated position following actuation of the trigger to deploy a fastener. The trigger may be coupled to a drive system 24 constructed and arranged to apply a deployment force to a fastener upon actuation of the trigger 12 to deploy the fastener from the distal end of the elongated shaft assembly 6. Moreover, in some embodiments, the surgical instrument may include an actuation lockout system 26 that may selectively prevent activation of the drive system 24 until a force applied to the trigger exceeds a threshold force. Although a specific drive system and actuation lockout system are shown in the figures, it should be understood that the current disclosure is not limited to surgical instruments including any particular drive systems and/or actuation lockout systems. For example, any appropriate arrangement of cams, linkages, gears, clutches, and other appropriate components may be used in any appropriate combination as part of a drive system.

According to some embodiments, a surgical instrument may include a plurality of fasteners within the elongated shaft assembly 6, and the fasteners may be deployed sequentially upon subsequent actuations of the trigger 12. In some such embodiments, it may be desirable to monitor the number of fasteners remaining within the elongated shaft assembly that have not yet been deployed. Accordingly, the surgical instrument 2 may include a fastener level indicator system 28 that is constructed and arranged to provide an indication of the number of fasteners available for deployment. For example, the fastener level indicator system 28 may be coupled to the trigger 12 such that upon actuation of the trigger (and deployment of a fastener), the fastener level indicator system may move a corresponding indicator to indicate that the number of fasteners remaining has decreased by one. However, it should be understood that other systems for monitoring the number of remaining fasteners also may be used, and that the surgical instrument may not include a fastener level monitoring system in some embodiments, as the disclosure is not limited in this regard.

In addition to the above, FIG. 2 depicts an articulation control system 100 according to some embodiments. The articulation control system may be coupled to the articulation control 10 and one or more shafts of the elongated shaft assembly 6 such that moving the articulation control 10 applies a suitable articulation force to one or more shafts, or other component of the elongated shaft assembly, to selectively move the articulable portion 8 of the elongated shaft assembly between at least an unarticulated and an articulated position. Moreover, in some embodiments, a single articulation control may be used to control multiple aspects of the articulation of the surgical instrument. For example, a surgical instrument may include an articulation lock to selectively permit or prevent articulation of the elongated shaft assembly. Accordingly, in some embodiments, a single integrated articulation control may be provided to allow a user to both selectively lock and unlock the articulation lock and control articulation of the articulable portion. However, it should be understood that other arrangements may be suitable. For example, in some embodiments, a surgical instrument may include a separate lock control for moving the articulation lock between the locked and unlocked positions. Accordingly, it should be understood that the current disclosure is not limited to any particular arrangement of articulation and/or lock controls to move an articulable portion of an elongated shaft assembly and/or articulation lock.

FIG. 3 depicts an exploded view of the elongated shaft assembly 6 of the surgical instrument 2 which extends distally from the handle 4. The elongated shaft assembly includes a drive shaft 30, which may be driven by a suitable drive system (such as drive system 24 discussed above) to apply a distally directed force to a fastener to deploy the fastener from the distal end of the elongated shaft assembly. The elongated shaft assembly further includes a first articulating shaft 32, which may be an inner articulating shaft, a second articulating shaft 34, which may be an outer articulating shaft, and an articulation lock in the form of a locking shaft 36. The first and second articulating shafts may be constructed and arranged to apply an articulation force to the elongated shaft assembly to move the articulable portion 8 between the non-articulated position and the one or more articulated positions. For example, in the depicted embodiment, the first and second articulating shafts may be arranged to apply an articulation force to the elongated shaft assembly upon application of opposing displacements to proximal portions of the first and second articulating shafts. In one embodiment, the first and second shafts may be axially fixed to one another at an attachment point located distally relative to the articulable portions, and the opposing displacements of the proximal portions may place the first and second articulating shafts in opposing states of compression and tension, which may result in a bending moment in the first and second articulating shafts that causes the shafts to bend towards the articulated configuration. Moreover, the locking shaft may be moveable (e.g. rotatable and/or slideable) between a locked configuration, in which the locking shaft prevents articulation of the elongated shaft assembly, and an unlocked configuration in which the locking shaft permits articulation.

Depending on the embodiment, an articulable portion of an elongated shaft assembly may be formed by one or more flexible portions of the associated shafts that permit articulation. For example, the flexible portions of the shafts may include a plurality of cuts extending across a width of the shafts and arranged along at least a portion of the length of the various shafts comprising the elongated shaft assembly to provide a desired flexibility. In some embodiments, the cuts may define a preferential bending direction for the articulable portion, and articulating the articulable portion may involve bending the articulable portion along the preferential bending direction. In other embodiments, the articulable portion may include one or more weakened sections arranged to create a desired flexibility and/or preferred bending direction, interconnected flexible segments, interconnected segments connected by hinges, one or more flexible shafts, or any other suitable structures, as the disclosure is not limited in this regard.

Moreover, it should be understood that the current disclosure is not limited to any particular arrangement for moving an articulable portion of an elongated shaft assembly to an articulated configuration, and that articulable portion may be constructed and arranged in any appropriate fashion to provide articulation in a desired direction. For example, in some embodiments, an articulation mechanism may include first and second articulating shafts with opposing spines that articulate the articulable portion when placed in opposing states of tension and compression. Alternatively, the articulable portion of the elongated shaft assembly may be articulated using: one or more control wires, ribbons, or slats associated with the articulable portion; pre-stressed members and retractable sheaths, rigid linkages associated with pivot joints; or any other appropriate structure capable of articulating the articulable portion.

As illustrated in FIG. 3, the various shafts of the elongated shaft assembly may be arranged coaxially relative to one another. For instance, in the depicted embodiment, the fastener carrier and follower assembly 38 is received within the driveshaft, which is received within the first and second articulating shafts 32, 34 and locking shaft 36. Although a particular arrangement of shafts is shown in the figures, it should be understood that other arrangements also may be suitable. For example, in one embodiment, the locking shaft 36 may be located within the first and second articulating shafts 32, 34. Accordingly, the current disclosure is not limited to any specific arrangement of shafts comprising the elongated shaft assembly.

In some embodiments, a fastener carrier (see FIGS. 6-7) and follower assembly 38 is provided within an elongated shaft assembly. For example, a stack 200 of fasteners 202 may be slidably disposed on a fastener carrier. The follower may be located proximally relative to the fastener stack 200 and may apply a distally directed force to one or more surgical fasteners of the stack to urge the stack of fasteners in the distal direction. Appropriate types of followers include, but are not limited to, compressed springs, ratchet and pawl mechanisms, walking beam assemblies, and/or any other appropriate type of mechanism capable of moving the stack of fasteners in a distal direction toward a distal end of the device.

Turing now to FIGS. 4-8, aspects of surgical fasteners which may be used with the articulating surgical instruments discussed above are described in more detail.

FIG. 4 is a schematic perspective view of one embodiment of a fastener 202, and FIG. 5 is a schematic cross-sectional side view of the same fastener. The fastener includes a head 204 at a proximal end of the fastener, a shaft 206 extending distally from the head, and a distal tip 208, which may be radially offset from a central longitudinal axis of the fastener. As illustrated, a through bore 210 extends through the fastener from a proximal surface of the head 204 through the shaft 206 such that it extends completely through the fastener head and shaft and exits at a distal end or portion of the fastener. As depicted in the figures, the distal tip may also be axially offset from the through bore as well. In some embodiments, the head of the fastener may have a non-circular cross sectional shape that includes a flat 212 constructed and arranged to engage a corresponding flat surface on the driveshaft, as discussed above, to maintain an orientation of the fastener within the driveshaft. Moreover, in some embodiments the fastener may include one or more barbs 214, which may aid in securing the fastener when it is deployed into tissue.

In some embodiments, the through bore 210 terminates at a sloped surface 216 at a distal end or distal portion of the shaft 206. For example, in the depicted embodiment, the sloped surface begins on a barb 214 and extends in a distal direction from an outer surface of the barb towards the distal tip, e.g., the sloped surface may slope inward from the barb in a distal direction towards the distal tip 208. The through bore exits the shaft through the sloped surface such that the sloped surface at least partially surrounds a distal opening of the through bore 210. Moreover, the sloped surface may terminate at a pair of shoulders 218 located on opposing sides of the through bore 210. For example, the shoulders 218 may be located on a planar surface adjacent the distal tip 208, and the planar surface may extend at least partially around the distal tip. The shoulders may have dimensions that are larger than a minimum dimension. As discussed previously, and without wishing to be bound by theory, such a configuration of a distal portion of the fastener 202 may aid in avoiding overly thin structures at the distal tip which may be susceptible to deflection and/or deformation when the distal tip is pressed into contact with a surface, such as during deployment into tissue.

It should be understood that the various features of a fastener may have any suitable dimensions, and in some instances, the dimensions may be chosen to avoid overly thin structures, such as at a distal tip of the fastener, which may be susceptible to deflection and/or deformation as noted above. For example, in one embodiment, a minimum thickness of the various fastener features, such as the shoulders, walls of a shaft adjacent an opening of a through bore, and/or at a distal tip, may be between 0.07 mm and about 0.20 mm (e.g., about 0.13 mm). Moreover, depending on the particular embodiment, a transverse dimension of the sloped surface at the two shoulders may be greater than or equal to about 0.05 mm, and a transverse dimension of the shaft is between or equal to about 0.25 mm and about 0.75 mm.

Depending on the particular embodiment, a sloped surface through which a through bore of a fastener exits may have any suitable shape. For example, in the depicted embodiment, the sloped surface 216 has a convex shape, though in other embodiments, the sloped surface may slope linearly towards the distal tip, have a concave shape, have multiple linear, concave and/or convex sections, and/or have any other appropriate shape as the disclosure is not limited in this regard.

As best illustrated in FIG. 5, in the depicted embodiment the through bore 210 extends entirely through the fastener from a proximal surface of the head 204 to the sloped surface 216 at the distal end of the shaft 206. Additionally, the fastener may include a recess 220 formed in the head 204. The recess is radially offset from the through bore 210, and as described below, the recess may be constructed and arranged to receive the distal tip 208 of an adjacent fastener when the fasteners are arranged in a stack within the surgical instrument. Without wishing to be bound by theory, such nesting of the distal tips within the recesses may reduce the stresses experienced by the distal tips when the fasteners are arranged in a fastener stack which may help avoid deformation and blunting of the tips, see FIG. 6. For example, a contact point between adjacent fasteners may be spaced from the distal tip and the contact area between adjacent fasteners may be increased to reduce the stress on the tips. In some embodiments, a transverse dimension of the recess 220 may be less than a transverse dimension of the planar surface on which the shoulders 218 are located. In such embodiments, the shoulders 218 of one fastener may contact the head 204 of an adjacent fastener at the opening of the recess and the recess may be deep enough such that the distal tip 208 received in the recess does not contact a distal inner surface of the recess.

In addition to the above, FIGS. 4-5 depict one possible structure for a distal tip 208 in which the distal tip has a blunt distal-most surface. In particular, the depicted distal tip 208 has a distal-most portion that is shaped as a truncated cone that extends distally from a larger diameter distally oriented flat located adjacent the shoulders 218. Similar to the shoulders, such a structure for the distal tip may help to avoid the presence of overly thin structures that may be deformed during deployment of the fastener. However, it should be understood that other structures for the distal tip 208 also may be suitable, including structures in which the distal tip is sharp. For example, in one embodiment the distal tip 208 may have a conical shape terminating at a sharp point.

Figure 6:
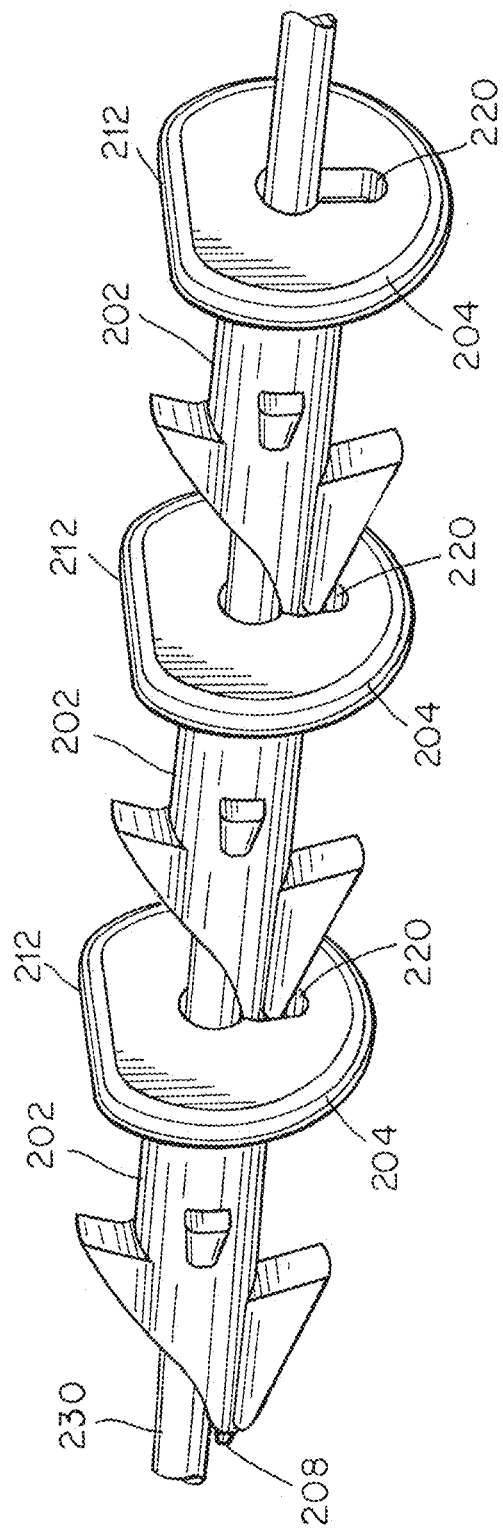
FIG. 6 is a perspective view of a portion of a fastener stack received on a fastener carrier, according to one embodiment.

FIG. 6 is a schematic perspective view of a stack of three fasteners 202 provided on a fastener carrier 230. For example, the fastener carrier may be used with the follower assembly 38 depicted in FIG. 3. In some embodiments, the fastener carrier may be an elongated shaft extending distally from a handle of a surgical instrument. As illustrated, the fastener carrier is slidably received through the through bores 210 of one or more fasteners 202, and the distal tips 208 of the surgical fasteners are received in recesses 220 formed in the heads 204 of adjacent fasteners as noted above.

Figure 7:
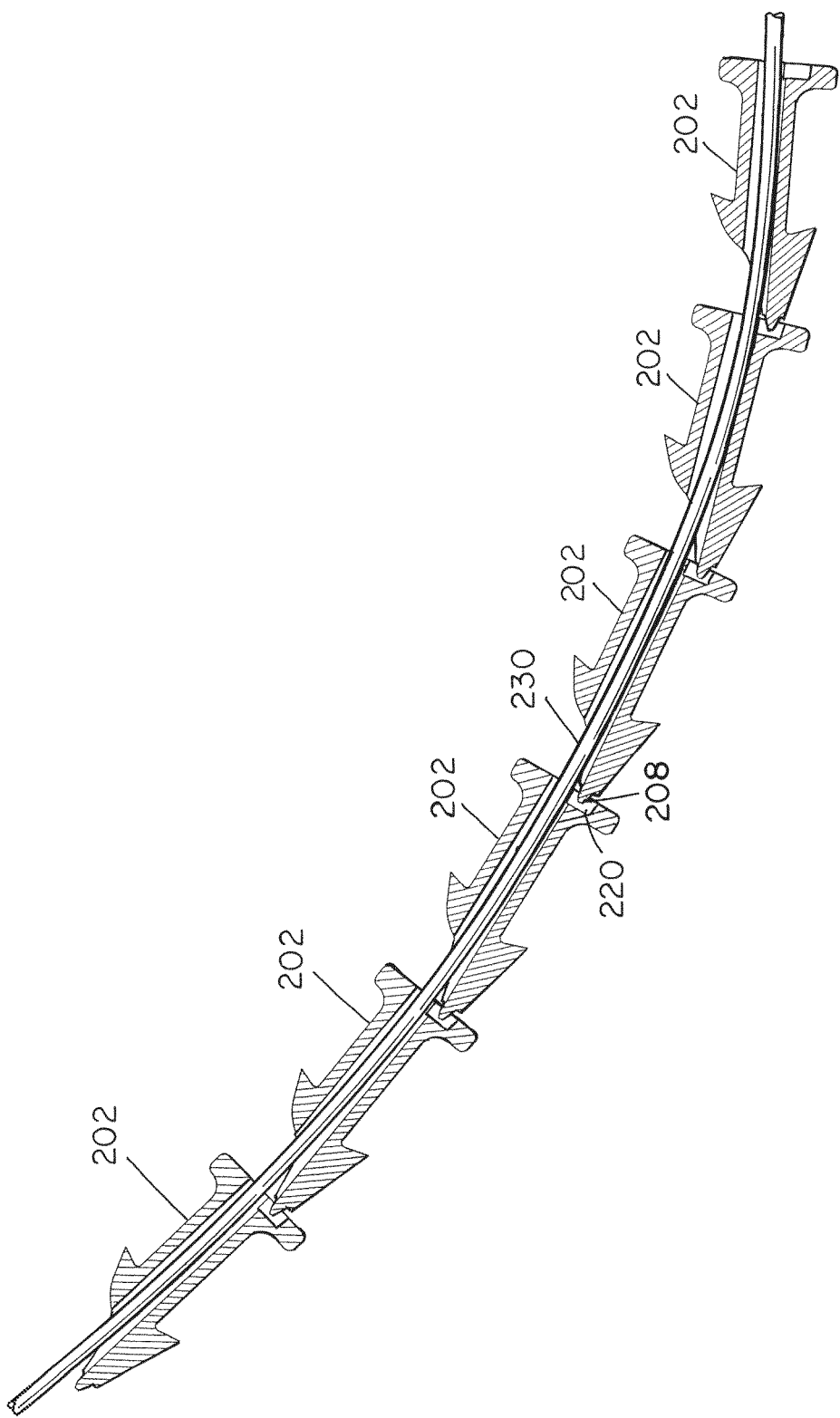
FIG. 7 is a cross-sectional side view of a portion of a fastener stack received on a fastener carrier with the fastener carrier in an articulated position, according to one embodiment.

FIG. 7 is a schematic cross sectional representation of a fastener stack similar to the stack shown in FIG. 6, but in a curved configuration corresponding to the elongated shaft assembly (including the fastener carrier 230) being moved to an articulated configuration. As illustrated in FIG. 7, with the distal tips 208 of the fasteners received in the recesses 220 of adjacent fasters, the fasteners are able to reorient relative to one another to accommodate the curved articulated position. For example, adjacent fasteners may be able to rotate relative to one another such that their respective longitudinal axes are oriented along different directions. In some embodiments, movement of the distal tips within the recesses may permit adjacent fasteners to be positioned at a range of angles relative to one another without binding on the fastener carrier 230 and/or without damaging the distal tips.

In addition to the above, FIG. 7 illustrates that when in the articulated configuration, a fastener carrier 230 may contact the through bores 210 of the fasteners 202 at one or more contact points. However, as discussed above, the inventors have appreciated that it may be desirable to limit the contact between the fastener carrier and the through bores to two or fewer contact points when in the articulated configuration. Without wishing to be bound by theory, such a configuration may reduce the possibility of the fasteners binding on the fastener carrier, which may limit the movement of the fasteners within the elongated shaft assembly and impede deployment of the fasteners.

Figure 8:
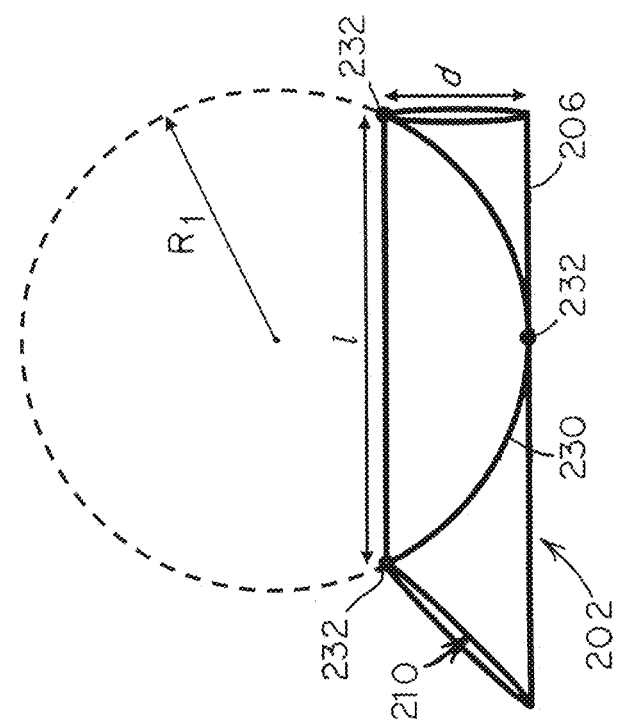
FIG. 8 is a schematic representation of a fastener and a portion of a fastener carrier, according to one embodiment.

In view of the above, in some embodiments, the dimensions of the fasteners may be chosen such that when the fastener carrier is in a curved configuration corresponding to the elongated shaft assembly being in the fully articulated position, the fastener carrier will have two or fewer contact points with the through bores of the fasteners. For example, FIG. 8 is a schematic depiction of a surgical fastener 202 and a portion of a fastener carrier 230 received in the through bore 210. The configuration shown in FIG. 8 may represent the limit of the dimensions of the through bore and the radius of curvature of the fastener carrier in which the fastener carrier contacts the through bore at three contact points 232. For instance, two contact points are at the ends of the through bore, and the third contact point is in the middle of the through bore. Accordingly, for a fastener 202 having a through bore transverse dimension (e.g. diameter) d and a shortest through bore length l, the radius of curvature $R_1$ of the fastener carrier 230 is a maximum radius of curvature resulting in three contact points. In one example, the radius $R_1$ may be equal to $$\frac{d}{2} + \frac{l^2}{8d}.$$

In view of the foregoing, in some embodiments, the dimensions d and l of the fastener and/or the radius of curvature of a fastener carrier in the fully articulated configuration may be chosen such that the radius of curvature of the fastener carrier is greater than $$\frac{d}{2} + \frac{l^2}{8d}.$$

Figure 9:
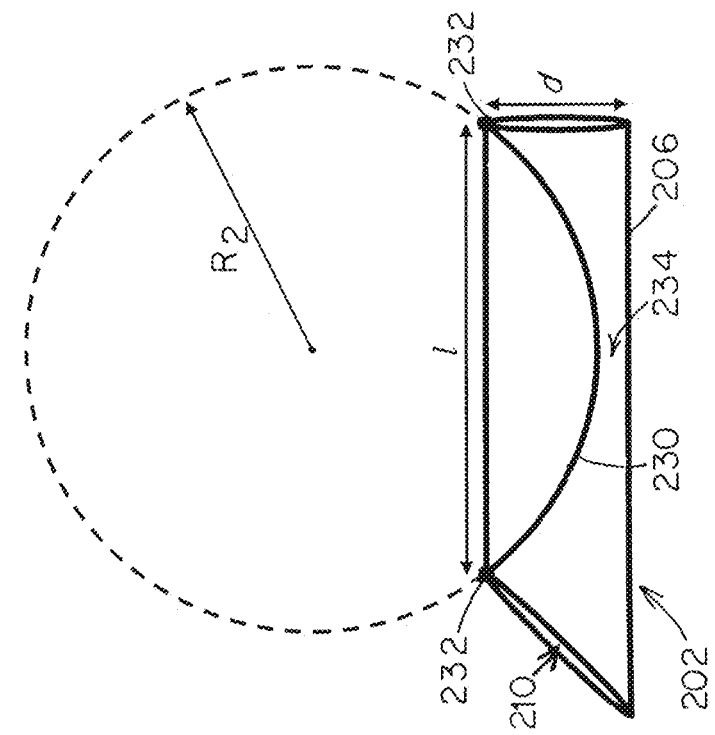
FIG. 9 is a schematic representation of a fastener and a portion of a fastener carrier, according to one embodiment.

Without wishing to be bound by theory, such dimensions may ensure that the fastener carrier 230 contacts the through bore 210 at two or fewer contact points 232. While this relationship does not account for the diameter of the fastener carrier, it provides a lower bound for a radius of curvature of the fastener carrier such that there will be two or fewer contact points. For example, FIG. 9 depicts one such embodiment in which the fastener 202 has the same dimensions d and l as in FIG. 8, but the fastener carrier 230 has a radius of curvature $R_2$ greater than $R_1$. For example, in certain embodiments, a fastener may have a through bore diameter d that is between 0.25 mm and 1.3 mm (e.g., about 0.75 mm), and a shortest through bore length l between about 4 mm and 6 mm (e.g., about 5 mm). Correspondingly, a portion of a fastener carrier received within the through bore may have a radius of curvature that is greater than at least about 4.5 mm. In one exemplary embodiment in which the through bore diameter d is about 0.75 mm, the shortest through bore length l is about 5 mm, and the fastener carrier has a diameter of about 0.6 mm, the minimum radius of curvature of the fastener carrier is about 30 mm. As a result, the fastener carrier contacts the through bore at two or fewer contact points and a clearance 234 is provided between the fastener carrier and the through bore within the through bore.

Figure 10:
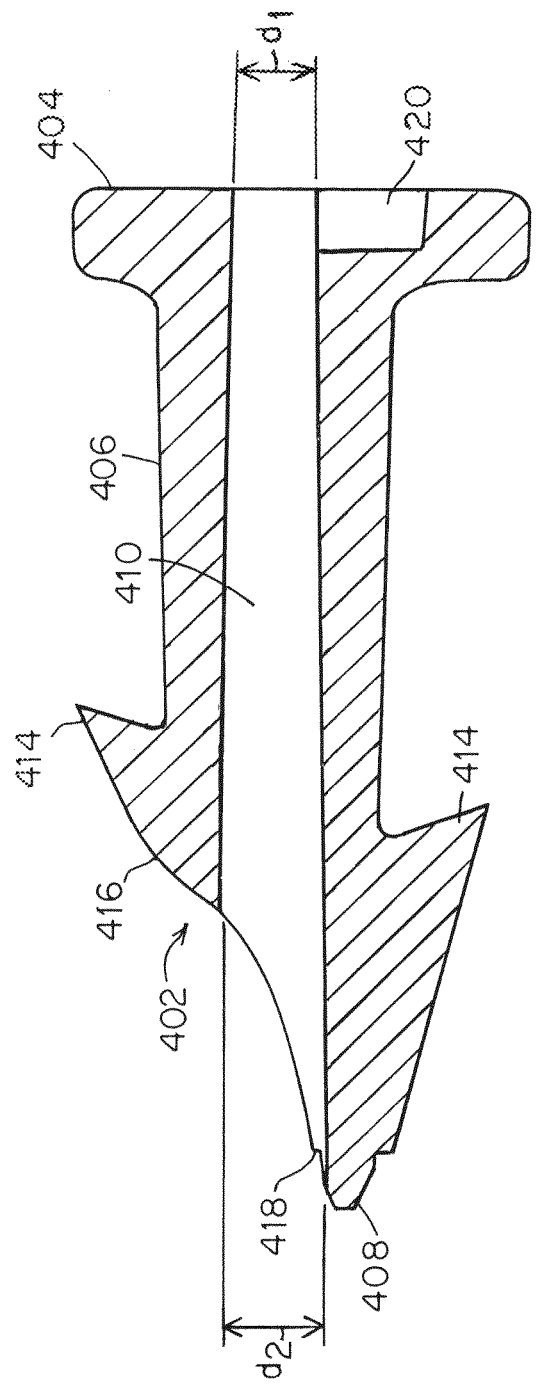
FIG. 10 is a cross-sectional side view of one embodiment of a surgical fastener.

Although FIGS. 4-9 depict fasteners having a generally cylindrical through bore, other configurations are envisioned. For example, FIG. 10 depicts a schematic cross-sectional side view of another embodiment of a fastener 402. Similar to the embodiments described above, the fastener 402 has a head 404, a shaft 406 extending distally from the head, and a distal tip 408. In the depicted embodiment, the shaft 406 has a tapered configuration, with a larger transverse dimension (e.g. a diameter) at the proximal end of the shaft (i.e., adjacent the head 404) and a smaller transverse dimension (e.g. a diameter) in a distal portion. A through bore 410 extends through the shaft 406 from a proximal surface of the head 404 to a distal end of the fastener, and terminates at a sloped surface 416, which slopes inward in a distal direction towards the distal tip 408. However, embodiments in which the through bore passes through a distal tip of the fastener and/or extends out of a different portion of the surgical fastener are also contemplated as the disclosure is not so limited. As illustrated in FIG. 10, the through bore 410 may have a tapered configuration, with a first transverse dimension (e.g. diameter) $d_1$ at a proximal end of the through bore and a second transverse dimension (e.g. diameter) $d_2$ at a distal end of the through bore. In the depicted embodiment, $d_1$ is smaller than $d_2$, though other configurations also may be suitable. Without wishing to be bound by theory, such a tapered configuration for the through bore may provide additional clearance for a fastener carrier received within the through bore when the carrier, and associated elongated shaft assembly, are in an articulated configuration, which may aid in avoiding binding of the fastener 402 on the fastener carrier.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical instrument comprising:
at least one articulable elongated shaft extending distally from a handle of a surgical instrument, wherein the at least one articulable elongated shaft is movable between a non-articulated configuration and a fully articulated configuration;
a fastener carrier disposed in and extending along at least a portion of a length of the at least one articulable elongated shaft; and
a fastener provided on the fastener carrier, the fastener comprising:
a head;
a shaft extending distally from the head; and
a through bore extending through the shaft from a proximal surface of the head to a distal portion of the shaft, wherein the fastener carrier is slidably received in the through bore, and wherein the through bore is sized and shaped to have two or fewer contact points with the fastener carrier when the at least one articulable elongated shaft and the fastener carrier disposed therein are in the fully articulated configuration.

2. The surgical instrument of claim 1, wherein the through bore has a transverse dimension d and a longitudinal dimension l, and, when the fastener carrier is in the fully articulated configuration, a radius of curvature of a portion of the fastener carrier within the through bore is greater than $$\frac{d}{2} + \frac{l^2}{8d}.$$

3. The surgical instrument of claim 1, wherein a first opening at a distal end of the through bore has a first transverse dimension that is larger than a second transverse dimension of a second opening at a proximal end of the through bore, and wherein the first opening is angled relative to a longitudinal axis of the through bore.

4. The surgical instrument of claim 1, wherein the fastener includes a recess formed in the proximal surface of the head and radially offset from a central axis of the through bore, and wherein the recess is constructed and arranged to receive a distal tip of an adjacent fastener.

5. The surgical instrument of claim 1, wherein the fastener further includes a sloped surface sloping toward a distal tip of the shaft, and wherein the distal tip is radially offset relative to the through bore.

6. The surgical instrument of claim 5, wherein the sloped surface is at least one selected from the group of curved and linear.

7. The surgical instrument of claim 1, wherein, when the fastener carrier is in the articulated configuration, a distal end of the fastener carrier is articulated at an angle of at least 45 degrees relative to the non-articulated configuration.

8. The surgical instrument of claim 1, wherein, when the fastener carrier is in the articulated configuration, a portion of the fastener carrier within the through bore has a radius of curvature of at least 30 mm.

9. A surgical instrument comprising:
a fastener carrier extending distally from a handle of a surgical instrument, the fastener carrier movable between a non-articulated configuration and a fully articulated configuration; and
a plurality of fasteners provided on the fastener carrier, wherein each fastener comprises:
a head;
a shaft extending distally from the head;
a through bore extending through the shaft from a proximal surface of the head to a distal portion of the shaft, wherein the fastener carrier is slidably received in the through bore; and
a recess formed in the proximal surface of the head and radially offset from a central axis of the through bore, and wherein the recess is constructed and arranged to receive a distal tip of an adjacent fastener.

10. The surgical instrument of claim 9, wherein the through bore is sized and shaped to have two or fewer contact points with the fastener carrier when the fastener carrier is in the fully articulated configuration.

11. The surgical instrument of claim 9, wherein a first opening at a distal end of the through bore has a first transverse dimension that is larger than a second transverse dimension of a second opening at a proximal end of the through bore, and wherein the first opening is angled relative to a longitudinal axis of the through bore.

12. The surgical instrument of claim 9, wherein each fastener further includes a sloped surface sloping toward a distal tip of the shaft, and wherein the distal tip is radially offset relative to the through bore.

13. The surgical instrument of claim 12, wherein the sloped surface extends from an outer surface of a barb towards the distal tip.

14. The surgical instrument of claim 12, wherein the recess is aligned with the distal tip.

15. The surgical instrument of claim 12, wherein the through bore passes through the sloped surface, wherein the sloped surface terminates at two shoulders located on opposing sides of the through bore, wherein a transverse dimension of the sloped surface at the two shoulders is greater than or equal to about 0.05 mm.

16. The surgical instrument of claim 12, wherein the sloped surface is at least one selected from the group of curved and linear.

17. A surgical instrument comprising:
a fastener carrier extending distally from a handle of a surgical instrument, the fastener carrier movable between a non-articulated configuration and a fully articulated configuration;
a fastener provided on the fastener carrier, the fastener comprising:
a head;
a shaft extending distally from the head; and
a through bore extending through the shaft from a proximal surface of the head to a distal portion of the shaft, wherein the fastener carrier is slidably received in the through bore, wherein the through bore has a first transverse dimension at a proximal end of the through bore and a second transverse dimension at a distal end of the through bore wherein the first transverse dimension is smaller than the second transverse dimension, and wherein the through bore tapers from the distal end of the through bore to the proximal end of the through bore, and wherein the shaft includes a distal tip, and wherein the distal tip is radially offset from the through bore.

18. The surgical instrument of claim 17, wherein the through bore is sized and shaped to have two or fewer contact points with the fastener carrier when the fastener carrier is in the fully articulated configuration.

19. The surgical instrument of claim 17, wherein, when the fastener carrier is in the articulated configuration, a distal end of the fastener carrier is articulated at an angle of at least 45 degrees relative to the non-articulated configuration.

20. The surgical instrument of claim 17, wherein, when the fastener carrier is in the articulated configuration, a portion of the fastener carrier within the through bore has a radius of curvature of at least 30 mm.

21. The surgical instrument of claim 17, wherein the fastener further includes a sloped surface sloping toward a distal tip of the shaft, and wherein the distal tip is radially offset relative to the through bore.

22. The surgical instrument of claim 21, wherein the through bore passes through the sloped surface, wherein the sloped surface terminates at two shoulders located on opposing sides of the through bore, and wherein the distal tip extends distally away from the two shoulders of the sloped surface.

23. The surgical instrument of claim 22, wherein the two shoulders are located on a planar surface adjacent the distal tip, and wherein the distal tip extends distally from the planar surface.

24. The surgical instrument of claim 23, wherein the planar surface extends at least partially around the distal tip.

25. The surgical instrument of claim 23, further comprising a recess formed on the proximal surface of the head, wherein the recess is constructed and arranged to receive a distal tip of an adjacent fastener in a fastener stack.

26. The surgical instrument of claim 25, wherein a transverse dimension of the recess is less than a transverse dimension of the planar surface.

\* \* \* \* \*